United States Patent
Venkataramani et al.

(10) Patent No.: US 11,972,584 B2
(45) Date of Patent: Apr. 30, 2024

(54) TISSUE SPECIFIC TIME GAIN COMPENSATION METHODS AND SYSTEMS

(71) Applicant: GE Precision Healthcare LLC, Wauwatosa, WI (US)

(72) Inventors: Rahul Venkataramani, Bangalore (IN); Krishna Seetharam Shriram, Bangalore (IN); Aditi Garg, Nagar (IN)

(73) Assignee: GE Precision Healthcare LLC, Wauwatosa, WI (US)

(*) Notice: Subject to any disclaimer, the term of this patent is extended or adjusted under 35 U.S.C. 154(b) by 393 days.

(21) Appl. No.: 17/488,750

(22) Filed: Sep. 29, 2021

(65) Prior Publication Data
US 2022/0101544 A1 Mar. 31, 2022

(30) Foreign Application Priority Data
Sep. 30, 2020 (IN) .............................. 202041042453

(51) Int. Cl.
*G06T 7/40* (2017.01)
*G06T 7/11* (2017.01)

(52) U.S. Cl.
CPC .................. *G06T 7/40* (2013.01); *G06T 7/11* (2017.01); *G06T 2207/10132* (2013.01); *G06T 2207/20021* (2013.01); *G06T 2207/20081* (2013.01); *G06T 2207/20084* (2013.01); *G06T 2207/30061* (2013.01); *G06T 2207/30084* (2013.01)

(58) Field of Classification Search
None
See application file for complete search history.

(56) References Cited

U.S. PATENT DOCUMENTS

2020/0330076 A1* 10/2020 Weber ................. G01S 7/52033

* cited by examiner

*Primary Examiner* — Leon Flores

(57) ABSTRACT

Systems and methods for tissue specific time gain compensation of an ultrasound image are provided. The method comprises acquiring an ultrasound image of a subject and displaying the ultrasound image over a console. The method further comprises selecting by a user a region within the ultrasound image that requires time gain compensation. The method further comprises carrying out time gain compensation of the user selected region of the ultrasound image. The method further comprises identifying a region having a similar texture to the user selected region and carrying out time gain compensation of the user selected region by an artificial intelligence (AI) based deep learning module.

19 Claims, 7 Drawing Sheets

TISSUE SPECIFIC TIME GAIN COMPENSATION METHODS AND SYSTEMS

CROSS-REFERENCE TO RELATED APPLICATIONS

This application claims the benefit of Indian Provisional Patent Application No. 202041042453, filed Sep. 30, 2020, the entire contents of which are hereby incorporated by reference for all purposes.

FIELD OF THE INVENTION

This disclosure relates generally to improved medical imaging systems and methods, and more particularly, to systems and methods for tissue specification time gain compensation of ultrasound images.

BACKGROUND OF THE INVENTION

Various medical imaging systems and methods are used to obtain the images of the affected regions of the subject for diagnosing the medical condition of the subject. Ultrasound imaging is a known medical imaging technique used for imaging the different body parts like joints, muscles vessels and pregnant woman (known as obstetric ultrasound). Ultrasound imaging offers several advantages over the other imaging techniques as the ultrasound is a real-time imaging technique that provides live stream of images. Commercially, the ultrasound devices are available in various configurations and the portable ultrasound devices are used for capturing the relatively bigger regions of the subject anatomy like uterus, lever, kidneys lower abdominal portions and lungs.

Ultrasound imaging involves generating and sending the ultrasound waves towards the portion of the subject body to be imaged and receiving the reflected waves from the subject body. Ultrasound imaging device consists of a probe that may be positioned on the skin of the subject over the portion of the pathology to be imaged. The probe emits the ultrasound waves into the body of the subject and the reflected waves may be captured to generate an image of the pathology of the subject. A user viewable ultrasound image is formed using the known image processing techniques.

During ultrasound imaging, as the ultrasound waves travel deep inside the subject organs, the ultrasound waves get attenuated and the reflected signal received from the deeper portions of the subject organ are significantly attenuated. Time-gain compensation (TGC) is a technique used to compensate for such depth induced signal attenuation in the ultrasound signals. Time gain compensation of the ultrasound signal includes artificially elevating the signal intensity with increasing depth and maintaining the same intensity irrespective of the depth of the acquisition. Further, the type of tissue being imaged also affects the level of signal attenuation and frequency of the transmitted signal for example a relatively low frequency signal will be more attenuated than a strong signal.

Time gain compensation (TGC) may be adjusted by the user of the ultrasound device based on his experience using a set of controls. While different TGC settings are available to the user, it may be difficult for a novice user to make these adjustments for better compensation. In one such method of time-gain compensation (TGC), the ultrasound image may be segmented into mainly three classes namely blood, tissue and noise and automated gain compensation may be carried out. However, such methods suffer from various drawbacks including lack of segmentation accuracy and using only three classes for segmentation. These segmentation techniques may result in under-compensating or over-compensating the signals.

Echogenicity of a tissue is a property of the tissue to reflect the ultrasound signals incident upon the tissue. Different tissues exhibit different textures and texture of the tissue defines the echogenicity of the tissue. Texture of a tissue type remains constant throughout its depth, but the amplitude of the signal reflected from the depth decays. The traditional approaches of anatomy-based segmentation may result in under segmentation as the anatomical regions may have sub-regions with different textures. In one example, the kidney cortex may have a different texture than the central portion of the kidney and time gain compensation of the kidney cortex based on the TGC values of the central portions of the kidney may result in erroneous compensation. Existing methods that use texture similarity are intensity based and may not address the issues like intensity variations due to texture template matching that usually has a single exemplar and therefore cannot account for natural variability. Accordingly, there is a need for a method that provides for time gain compensation of the images based on the texture of the individual tissues of the organs rather than the anatomy-based segmentation.

BRIEF DESCRIPTION OF THE INVENTION

In accordance with an aspect of the disclosure a method is disclosed for tissue specific time gain compensation of an ultrasound image. The method comprises acquiring the ultrasound image of a subject and displaying the ultrasound image over a console. The method further comprises selecting by a user a region within the ultrasound image that requires time gain compensation. The method further comprises carrying out time gain compensation of the user selected region of the ultrasound image.

In accordance with an aspect of the disclosure a system is disclosed for tissue specific time gain compensation of an ultrasound image. The system comprises an ultrasound probe configured acquire the ultrasound image of a subject organ. The system further comprises a computer system connected to the ultrasound probe and configured to acquire the plurality of images of the subject organ. The computer system comprises a processor; a memory connected to the processor and configured to store the ultrasound images of the subject organ and an artificial intelligence (AI) based deep learning module employed on the memory. The system further comprises a console connected to the computer system and configured to display the ultrasound images acquired by the ultrasound probe. When a user of the system selects a region within the ultrasound image that requires time gain compensation, the AI based deep learning module carries out time gain compensation of the user selected region of the ultrasound image and displays a time gain compensated image over the console.

DETAILED DESCRIPTION

Figure 1:
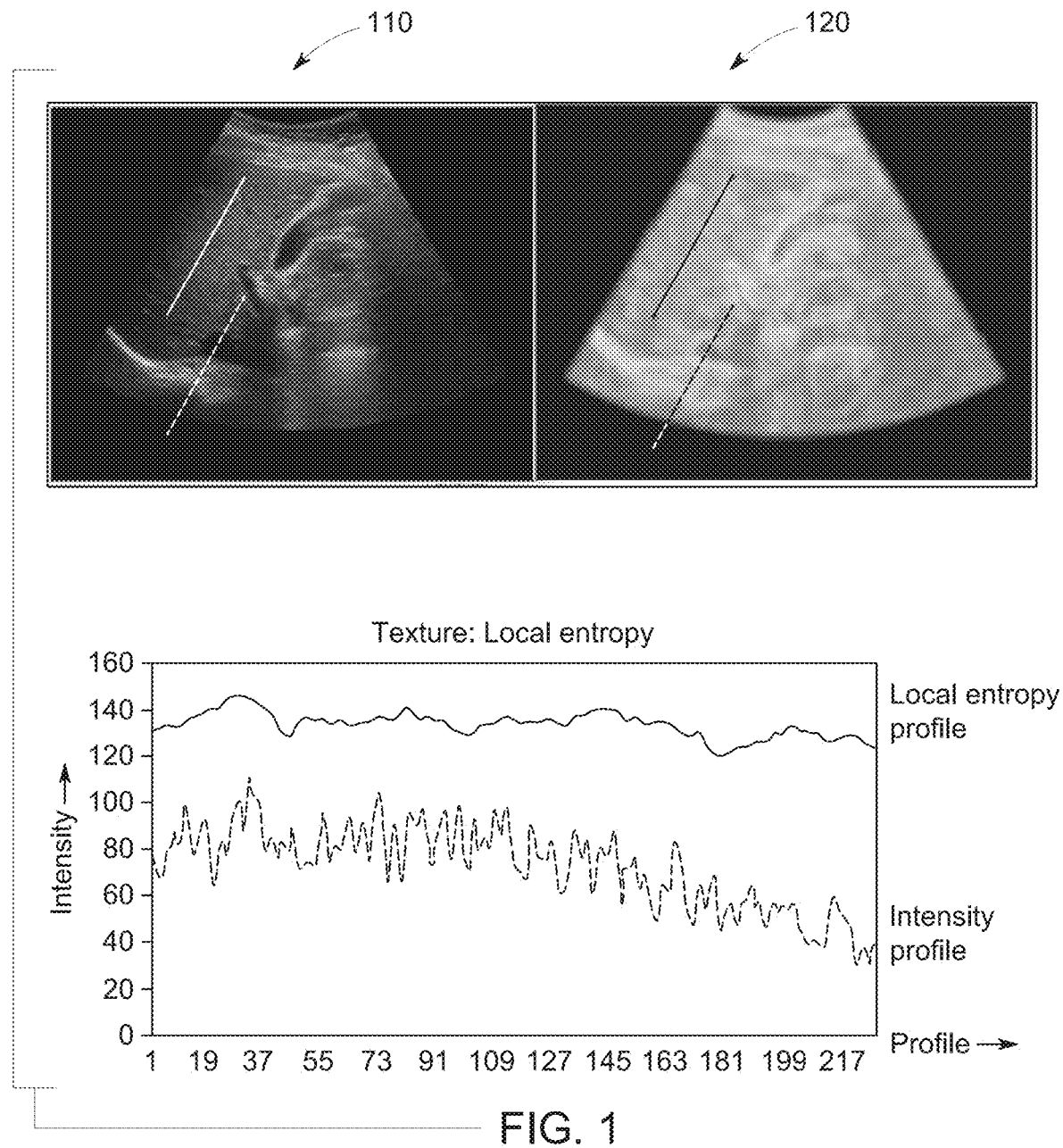
FIG. 1 illustrates change in intensity and texture profile of a liver tissue over acquisition depth in an ultrasound image according to an embodiment of the disclosure.

In the following specification and the claims, reference will be made to a number of terms, which shall be defined to have the following meanings.

The singular forms "a", "an", and "the" include plural references unless the context clearly dictates otherwise.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

As used herein, the terms "software" and "firmware" are interchangeable, and include any computer program stored in memory for execution by devices that include, without limitation, mobile devices, clusters, personal computers, workstations, clients, and servers.

As used herein, the term "computer" and related terms, e.g., "computing device", "computer system" "processor", "controller" are not limited to integrated circuits referred to in the art as a computer, but broadly refers to at least one microcontroller, microcomputer, programmable logic controller (PLC), application specific integrated circuit, and other programmable circuits, and these terms are used interchangeably herein.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

In accordance with an aspect of the disclosure a method is disclosed for tissue specific time gain compensation of an ultrasound image. The method comprises acquiring the ultrasound image of a subject and displaying the ultrasound image over a console. The method further comprises selecting by a user a region within the ultrasound image that requires time gain compensation. The method further comprises carrying out time gain compensation of the user selected region of the ultrasound image.

In accordance with an aspect of the disclosure a system is disclosed for tissue specific time gain compensation of an ultrasound image. The system comprises an ultrasound probe configured acquire the ultrasound image of a subject organ. The system further comprises a computer system connected to the ultrasound probe and configured to acquire the plurality of images of the subject organ. The computer system comprises a processor; a memory connected to the processor and configured to store the ultrasound images of the subject organ and an artificial intelligence (AI) based deep learning module employed on the memory. The system further comprises a console connected to the computer system and configured to display the ultrasound images acquired by the ultrasound probe. When a user of the system selects a region within the ultrasound image that requires time gain compensation, the AI based deep learning module carries out time gain compensation of the user selected region of the ultrasound image and displays a time gain compensated image over the console.

Embodiments of the present disclosure will now be described, by way of example, with reference to the figures, in which FIG. 1 shows change in intensity and texture profile of a liver tissue over acquisition depth in an ultrasound image (100). As may be seen from the original image (110), during ultrasound imaging, as the ultrasound wave travels deep inside the subject liver, the ultrasound waves get attenuated and the signal received from the deeper portions of the subject liver are significantly attenuated. As the ultrasound wave goes deeper into the liver tissue, the intensity (120) of the reflected ultrasound signal reduces. Such images require time-gain compensation (TGC) to compensate for depth induced signal attenuation in the ultrasound signals. Time gain compensation of the ultrasound signal includes artificially elevating the signal intensity with increasing depth and maintaining the same intensity irrespective of the depth of the acquisition. Further, the type of tissue being imaged also affects the level of signal attenuation and frequency of the transmitted signal for example a relatively low frequency signal will be more attenuated than a strong signal.

Figure 2:
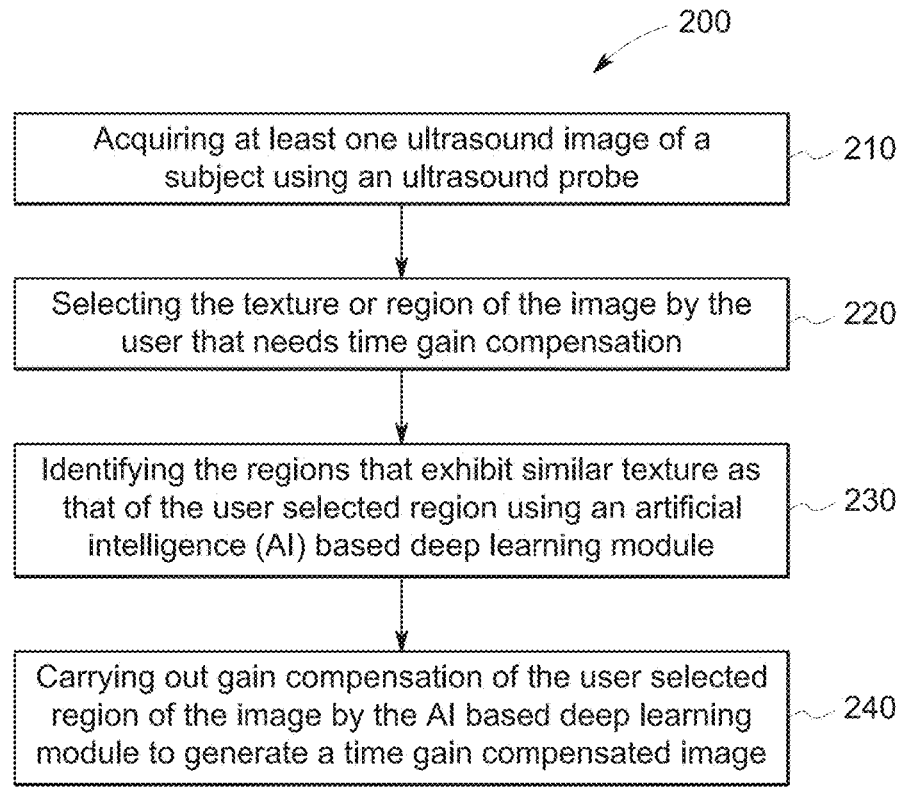
FIG. 2 illustrates a method for tissue specific time gain compensation according to an embodiment of the disclosure.

In accordance with an aspect of the disclosure, FIG. 2 shows a method (200) for tissue specific time gain compensation. The method (200) comprises acquiring (210) at least one ultrasound image of a subject using an ultrasound probe. Once the ultrasound image is acquired, the user/viewer of the image may observe the image for loss of intensity along the depth of the tissue/organ being imaged. The method (200) comprises selecting (220) the texture or region of the image by the user that needs time gain compensation. In one example, selecting (220) the region of the image by the user may include clicking on the image area that requires time gain compensation. The method (200) further comprises identifying (230) the regions that exhibit similar texture as that of the user selected region using an artificial intelligence (AI) based deep learning module. In one example, the AI based deep learning module may be configured to identify the regions that exhibit the similar texture. The AI based deep learning module may be configured to automatically segment the ultrasound image into the regions with similar texture. The regions exhibiting similar texture may be located at different depths and need compensation for obtaining a consistent image. According to an aspect of the disclosure, the image texture may be a marker of echogenicity that is invariant to the acoustic shadows as well as to the signal drop-off with the increasing depth. The method (200) further comprises carrying out (240) gain compensation of the user selected region of the image by the AI based deep learning module to generate a time gain compensated image. The regions in an image that exhibit similar texture may be compensated simultaneously to obtain brightness consistency.

Figure 3A:
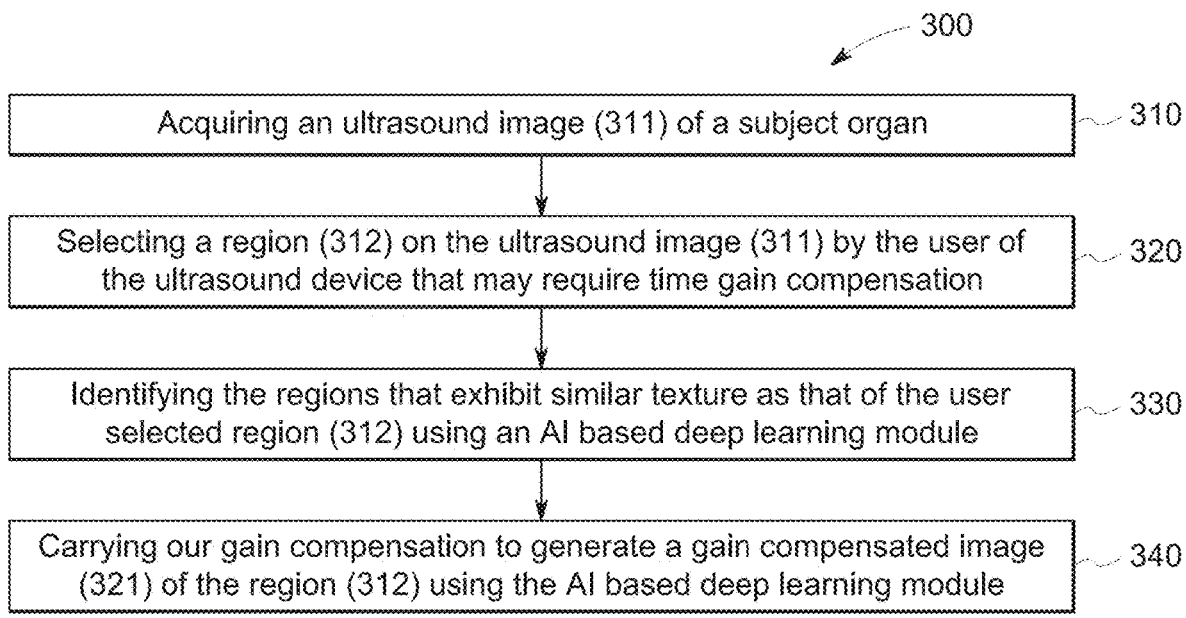
FIG. 3(a) illustrates a method for tissue specific time gain compensation for a liver according to an embodiment of the disclosure.
Figure 3B:
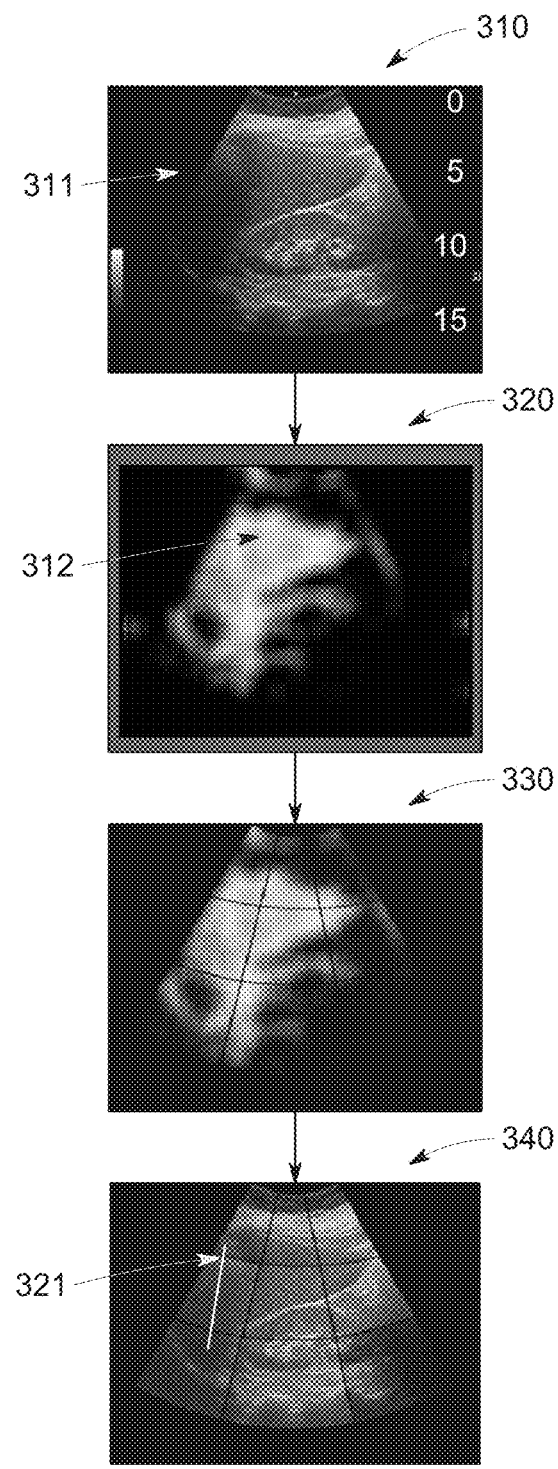
FIG. 3(b) illustrates a workflow of the method for tissue specific time gain compensation illustrated in FIG. 3(a) according to an embodiment of the disclosure.

In accordance with an aspect of the disclosure, FIGS. 3(a) and 3(b) show an example of the method (300) for tissue specific time gain compensation for image of the subject liver. The method (300) includes acquiring (310) an ultrasound image (311) of the liver of the subject using an ultrasound probe. The method (300) further includes selecting (320) a region (312) on the ultrasound image (311) by the user of the ultrasound device that may require time gain compensation. During ultrasound imaging, as the ultrasound wave travels deep inside the subject liver, the ultrasound waves get attenuated and the signal received from the deeper portions of the subject liver are significantly attenuated. As the ultrasound wave goes deeper into the liver tissue, the intensity of the reflected ultrasound signal reduces. Such images require time-gain compensation (TGC) to compensate for depth induced signal attenuation in the ultrasound signals. The method (300) further includes identifying (330) the regions that exhibit similar texture as that of the user selected region (312) using an AI based deep learning module. The method (300) further includes carrying out (340) gain compensation of the user selected region (312) of the ultrasound image of the liver by the AI based deep learning module to generate a time gain compensated image and output the gain compensated image. It may be observed that the user selected region (312) in the gain compensated image is brighter than the originally acquired image (311). During the time gain compensation of the selected region (312), the method (300) may include dividing the ultrasound image into a grid view of for example three depths and three lateral views using the AI based deep learning module. Further, in each of the grid there may be an intensity variation and the AI module may identify the mean intensity of each grid. The AI module may shift the intensity mean to match the lowest depth of the grid. Method (300) further includes generating (340) a gain compensated image (321) of the region (312) using the AI based deep learning module.

Figure 3C:
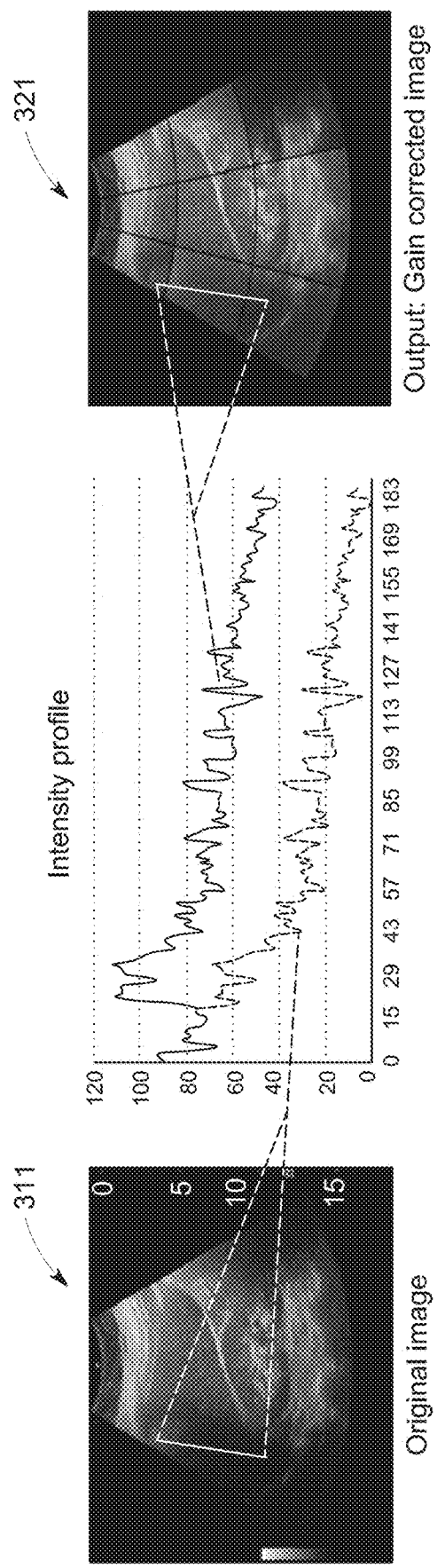
FIG. 3(c) illustrates an intensity profile of the original ultrasound image and the time gain compensated image generated using an AI based deep learning module according to an embodiment of the disclosure.

In accordance with an aspect of the disclosure, FIG. 3(c) shows an intensity profile of the original ultrasound image and the time gain compensated image generated using an AI based deep learning module. It may be observed that the intensity values of the time gain compensated image (321) are higher than the originally acquired ultrasound image (311). The improvement in intensity in the TGC image (321) is due to the compensation of the user selected region (312) by the AI based deep learning module. Further, the grid view of the TGC image (321) substantially improves the intensity only of the user selected region and other grid portions may be ignored.

In one example, the AI based deep learning module may include a siamese network for iso-texture segmentation that may be trained to evaluates similarity of a pair of inputs. This network may be used to identify similarities in the texture between the user selected region of the image and the other regions exhibiting similar texture and compensate the user selected region. Different anatomical regions exhibit myriad texture patterns within the regions. In one example discussed above, the liver contains vascular cross-sections with starkly different textures. Accordingly, carrying our organ-based segmentation may lead to uniform compensation of the entire organ irrespective of the different textures present within the organ and the images generated by such segmentation would not be specific. Further, the traditional AI based modules that are trained using the organ specific segmentation carry huge annotation burden to generate labelled training datasets across all the organs and ack of known anatomical context leads to suboptimal segmentation results being produced by the AI modules. These limitations in training the AI module with the correct segmentation may be avoided using the texture-based segmentation of the organs. Further, mere presence of the texture may suffice for segmentation of the tissues without requirement for anatomical context by the AI module. Accordingly, organ-based segmentation may be done away with for faster training of the AI module and analysis of the image data. Further, the AI algorithm may be trained for performing the texture similarity and can infer to potentially evaluate similarity between the pairs of previously unseen texture patterns and the AI algorithm may not require elaborate manual annotation for training.

Terms deep learning (DL), machine learning (ML) and artificial intelligence (AI) are correlated and often used interchangeably. However, artificial intelligence is a relatively broader technology that covers intelligent machines with thinking capability and machine learning includes learning from data.

Deep learning is a class of machine learning techniques employing representation learning methods that allows a machine to be given raw data and determine the representations needed for data classification. Deep learning ascertains structure in data sets using backpropagation algorithms. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine operating conditions. A neural network behaves in a certain manner based on its own sequences. Learning refines the machine output, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the system for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, for example. This set of data builds the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as conditions for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for image analysis. Stages of CNN analysis can be used for facial recognition in natural images, computer-aided diagnosis (CAD), etc.

Interpretation of medical images, regardless of quality, is only a recent development. Medical images are largely interpreted by physicians, but these interpretations can be subjective, affected by the condition of the physician's experience in the field and/or fatigue. Image analysis via machine learning can support a healthcare practitioner's workflow.

Deep learning machines can provide computer aided detection support to improve their image analysis with respect to image quality and classification, for example. However, issues facing deep learning machines applied to the medical field often lead to numerous false classifications. Deep learning machines must overcome small training datasets and require repetitive adjustments, for example.

Deep learning machines, with minimal training, can be used to determine the quality of a medical image, for example. Semi-supervised and unsupervised deep learning machines can be used to quantitatively measure qualitative aspects of images. For example, deep learning machines can be utilized after an image has been acquired to determine if the quality of the image is enough for diagnosis. Supervised deep learning machines can also be used for computer aided diagnosis. Supervised learning can help reduce susceptibility to false classification, for example.

Deep learning machines can utilize transfer learning when interacting with physicians to counteract the small dataset available in the supervised training. These deep learning machines can improve their computer aided diagnosis over time through training and transfer learning.

Figure 4:
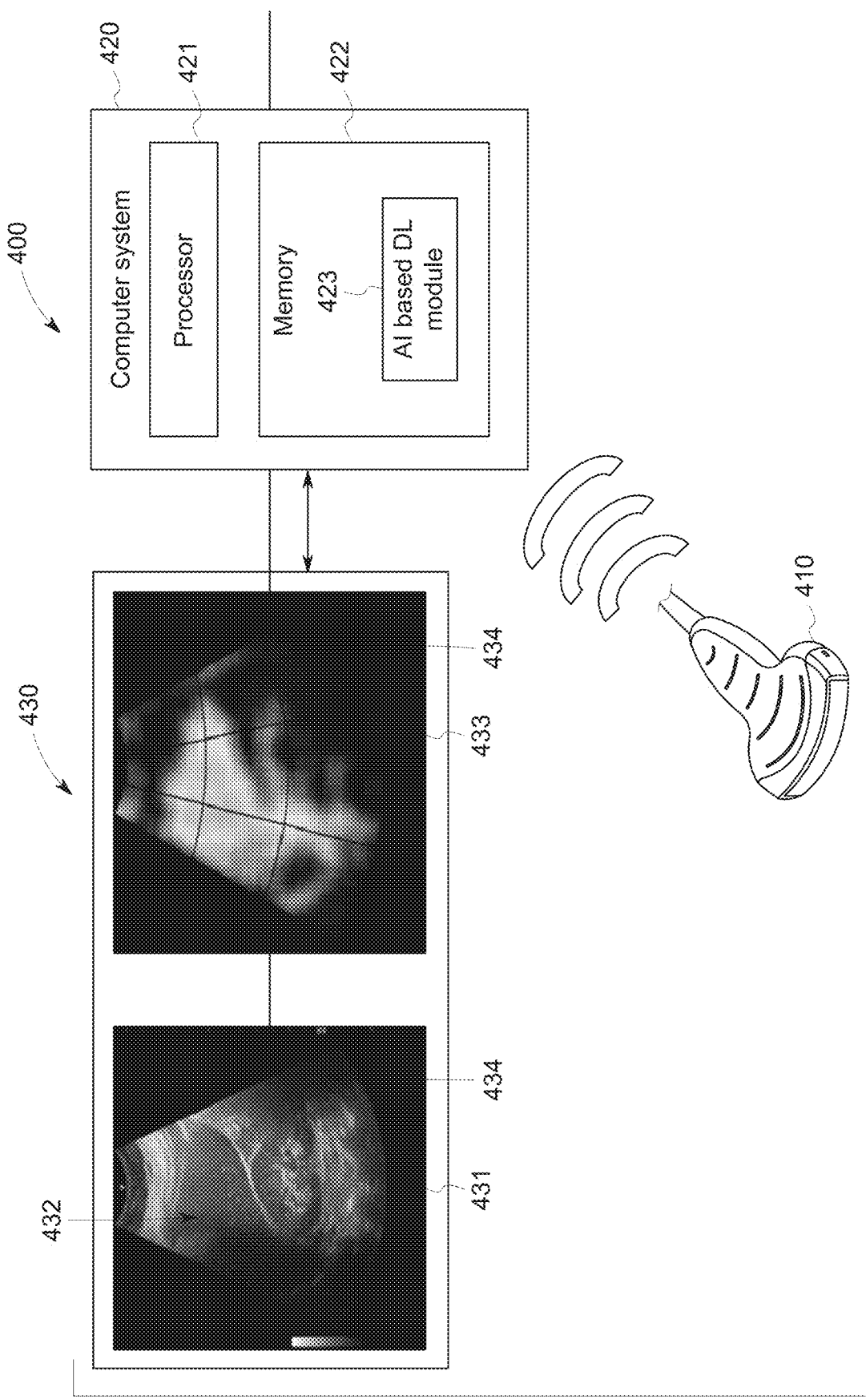
FIG. 4 illustrates a system for tissue specific time gain compensation of an ultrasound image according to an embodiment of the disclosure.

In accordance with an aspect of the disclosure, FIG. 4 shows a system (400) for tissue specific time gain compensation of an ultrasound image. The system (400) includes an ultrasound probe (410) configured to send ultrasound waves towards the subject organ to be imaged. The ultrasound probe (410) includes transducers configured to receive the reflected ultrasound signals from the subject organ. The ultrasound probe (410) may be connected to a computer system (420) and adapted to receive the ultrasound image data from the ultrasound probe (410). The computer system (420) may include a processor (421), a memory (422), and at least one artificial intelligence module (423) deployed over the memory (422). The artificial intelligence module (423) may be a deep learning module that may be trained to identify the texture of the user selected region and identify other regions from the images of the subject body that exhibit similar texture. The artificial intelligence module (423) may be configured to generate a time gain compensated image for the region selected by the user. The system (400) may include a console (430) for a user to view the images and provide user selection. The console (430) may be connected to the computer system (420). In one example, the console (430) may be a display screen or a touch screen and the original ultrasound image (431) of the subject liver may be displayed to the user. The user may view the image and select a region (432) that may require time gain compensation. The user selected region (432) may be communicated to the AI based deep learning module (423) on the computer system (420) for processing the region (432) for time gain compensation. The AI based deep learning module (423) may include a siamese network for iso-texture segmentation that may be trained to evaluates similarity of a pair of inputs. This network may be used to identify similarities in the texture between the user selected region of the image and the other regions exhibiting similar texture and carry out time gain compensation of the user selected region (432). Different anatomical regions exhibit myriad texture patterns within the regions. In one example discussed above, the liver contains vascular cross-sections with starkly different textures. Accordingly, carrying our organ-based segmentation may lead to uniform compensation of the entire organ irrespective of the different textures present within the organ and the images generated by such segmentation would not be specific. Further, the traditional AI based modules that are trained using the organ specific segmentation carry huge annotation burden to generate labelled training datasets across all the organs and ack of known anatomical context leads to suboptimal segmentation results being produced by the AI modules. These limitations in training the AI module with the correct segmentation may be avoided using the texture-based segmentation of the organs. Further, mere presence of the texture may suffice for segmentation of the tissues without requirement for anatomical context by the AI module. Accordingly, organ-based segmentation may be done away with for faster training of the AI module and analysis of the image data. Further, the AI algorithm may be trained for performing the texture similarity and can infer to potentially evaluate similarity between the pairs of previously unseen texture patterns and the AI algorithm may not require elaborate manual annotation for training. The AI based deep learning module (423) may output a time gain compensated image (433) to the subject over the console (430). In one example, in case of the ultrasound image (431) of the liver, the AI based deep learning module (423) may be configured to identify only the textures that correspond to the subject lever and carry out time gain compensation. If the region, for example region (434) that is not identified as a liver portion may be left untouched by the AI based deep learning module (423) and no time gain compensation is carried out for region (434).

Figure 5:
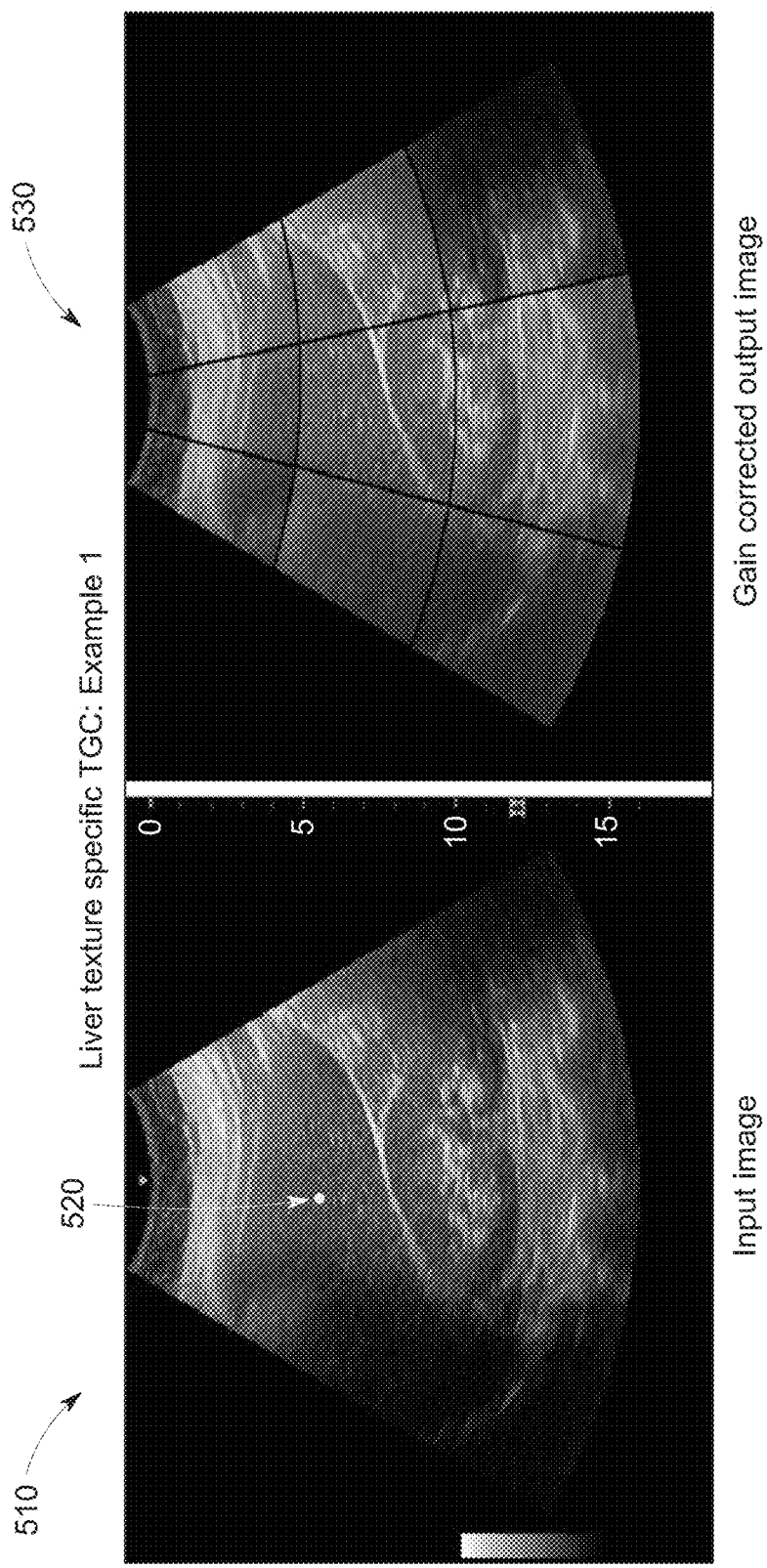
FIG. 5 illustrates an example of the texture specific time gain compensation of the ultrasound image of the liver tissue according to an embodiment of the disclosure.

In accordance with an aspect of the disclosure, FIG. 5 shows an example of the texture specific time gain compensation of the ultrasound image of the liver tissue. In the current example, the liver tissue image (510) is an original image obtained using the ultrasound scanning device according to an aspect of the disclosure. When the viewer/user of the ultrasound device observes loss of brightness in the image as the depth of the tissue increases, the user may require time gain compensation of the image (510) at any region (520) of the image. Accordingly, the user may select the region (520) for time gain compensation. In one example, the user may click on the region (520) of the image (510) to identify the region that requires time gain compensation. The region (520) may be processed for time gain compensation by the AI based deep learning module discussed with respect to FIG. 4 and identify the regions that exhibit similar texture. Once the regions with similar texture are identified, the AI based deep learning module may carry out time gain compensation of the region (520). During the time gain compensation of the region (520), the AI based deep learning module may divide the image into a grid view of three depths and three lateral views. Further, in each of the grid there may be an intensity variation and the AI module may identify the mean intensity of each grid. The AI module may shift the intensity mean to match the lowest depth of the grid. Further, the AI module may generate a gain compensated image (530).

Figure 6:
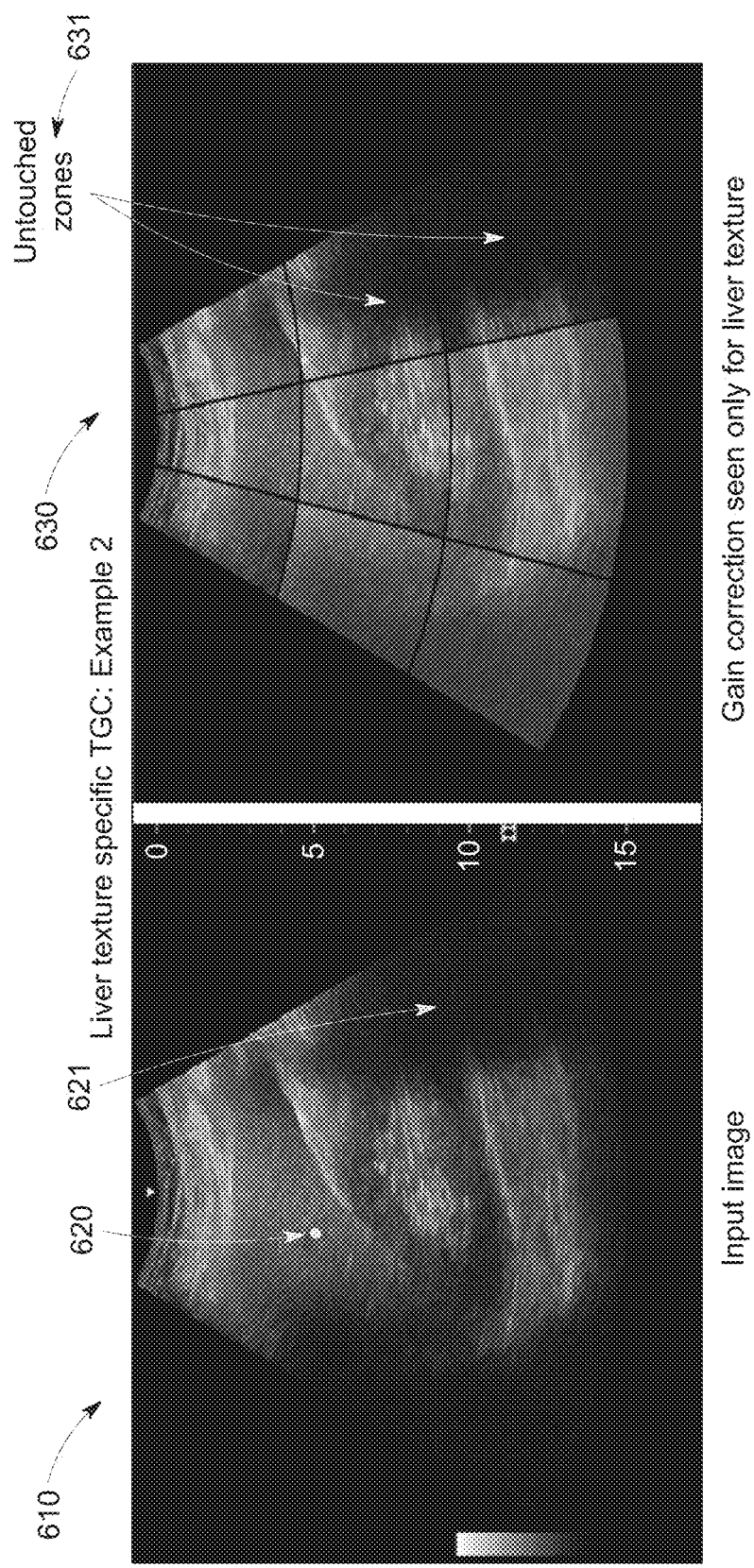
FIG. 6 illustrates an example of the texture specific time gain compensation of an ultrasound image of the liver tissue according to an embodiment of the disclosure.

In accordance with an aspect of the disclosure, FIG. 6 shows an example of the texture specific time gain compensation of an ultrasound image of the liver tissue. In the current example, the liver tissue image (610) is an original image obtained using the ultrasound scanning device according to an aspect of the disclosure. When the viewer/user of the ultrasound device observes loss of brightness in the image as the depth of the tissue increases, the user may require time gain compensation of the image (610) at any region (620) of the image. Accordingly, the user may select the region (620) for time gain compensation. In one example, the user may click on the region (620) of the image (610) to identify the region that requires time gain compensation. Clicking by the user on the region (620) may be using a computer cursor or using a touch screen technology, however, any other means for selecting the region (620) are within the scope of the disclosure. The region (620) may be processed for time gain compensation by the AI based deep learning module discussed with respect to FIG. 4 and identify the regions that exhibit similar texture. Once the regions with similar texture are identified, the AI based deep learning module may carry out time gain compensation of the region (620). During the time gain compensation of the region (620), the AI based deep learning module may divide the image into a grid view of three depths and three lateral views. Further, in each of the grid there may be an intensity variation and the AI module may identify the mean intensity of each grid. The AI module may shift the intensity mean to match the lowest depth of the grid. Further, the AI module may generate a gain compensated image (630). According to an aspect of the disclosure, if the user or the AI module observes that the tissues in the region (621) are not liver tissues and do not require time gain compensation, the region (621) may not be processed for time gain compensation. The time gain compensated image (630) has an untouched region (631) that is not processed by the AI module for time gain compensation.

Some of the advantages of the method of the present disclosure provide the user of the ultrasound device an option to click a single point in the image to specify the tissue type that requires further gain compensation. Single click on the image replaces the multiple dials that were necessary to be adjusted for TGC. The image processing workflow may not impacted even if the acquisition depth is changed, unlike in conventional systems where dials must be tuned again. Further, the AI algorithm in the background will cluster regions of similar echogenicity as the specified point and apply the necessary compensation. Additionally, the method according to the present disclosure provides user with more control on the specific regions of the image where compensation may be performed, unlike auto-TGC where no user input is possible.

From the foregoing, it will be appreciated that the above disclosed methods, and systems have been disclosed to monitor, process, and improve operation of imaging and/or other healthcare systems using a plurality of deep learning and/or other machine learning techniques. Although certain example methods, and systems have been described herein, the scope of coverage of this disclosure is not limited thereto. On the contrary, this disclosure covers all methods, apparatus and articles of manufacture fairly falling within the scope of the claims of this patent.

We claim:

1. A method for tissue specific time gain compensation of an ultrasound image, the method comprising: acquiring the ultrasound image of a subject and displaying the ultrasound image over a console; selecting by a user a region within the ultrasound image that requires time gain compensation; and carrying out time gain compensation of the region of the ultrasound image selected by the user using an artificial intelligence (AI) based deep learning module.

2. The method of claim 1 wherein selecting by the user the region within the ultrasound image comprises identifying by the user the region within the ultrasound image that requires time gain compensation and clicking on the region using a cursor of the console.

3. The method of claim 1 wherein carrying out time gain compensation of the user selected region of the ultrasound image comprises:
   identifying a texture of the user selected region;
   identifying a region having a similar texture to the user selected region; and
   carrying out time gain compensation of the user selected region.

4. The method of claim 3 wherein identifying a region having a similar texture to the user selected region comprises clustering the regions of similar echogenicity as that of the user selected region.

5. A method for tissue specific time gain compensation of an ultrasound image, the method comprising: acquiring the ultrasound image of a subject and displaying the ultrasound image over a console; selecting by a user a region within the ultrasound image that requires time gain compensation; and carrying out time gain compensation of the region of the ultrasound image selected by the user, wherein carrying out time gain compensation of the user selected region comprises dividing the ultrasound image to generate a grid portions and shifting the intensity mean of the grid corresponding to the user selected region to match a lowest depth of the user selected region.

6. The method of claim 5 further comprising ignoring the grid portions that have a different texture than the user selected region.

7. The method of claim 1 wherein carrying out time gain compensation of the user selected region of the ultrasound image comprises segmenting the ultrasound image based on an image texture without reference to the anatomical context.

8. A method for tissue specific time gain compensation, the method comprising: obtaining an ultrasound image of a subject and displaying the ultrasound image over a console; selecting by a user a region within the ultrasound image that requires time gain compensation; employing an artificial intelligence (AI) based deep learning module configured to identify a texture of the user selected region and at least one region within the ultrasound image that exhibits a similar texture; carrying out time gain compensation of the user selected region and the at least one region within the ultrasound image that exhibits the similar texture of the ultrasound image to obtain brightness consistency between the user selected region and the at least one region within the ultrasound image that exhibits the similar texture; and displaying a gain compensated image on the console.

9. The method of claim 8 further comprising employing the AI based deep learning module and configuring the AI based deep learning module for identifying a region from a set of training ultrasound images stored on a computer memory that exhibits the similar texture to that of the user selected region.

10. The method of claim 9 wherein identifying a region from a set of training ultrasound images stored on a computer memory that exhibits the similar texture to that of the user selected region comprises clustering the regions that exhibit similar echogenicity as that of the user selected region.

11. The method of claim 1 wherein displaying a gain compensated image on the console comprises dividing the gain compensated image into a plurality of grid portions and shifting the intensity mean of the plurality of the grid portions corresponding to the user selected region to match a lowest depth of the user selected region.

12. The method of claim 1 wherein carrying out time gain compensation of the user selected region of the ultrasound image comprises carrying out time gain compensation of only the grid portions that correspond to the user selected region.

13. The method of claim 12 further comprising ignoring the grid portions that have a texture different than the texture of the user selected region.

14. A system for tissue specific time gain compensation of an ultrasound image, the system comprising:
   an ultrasound probe configured acquire the ultrasound image of a subject organ;
   a computer system connected to the ultrasound probe and configured to acquire the plurality of images of the subject organ, wherein the computer system comprises:
      a processor;
      a memory connected to the processor and configured to store the ultrasound images of the subject organ;
      an artificial intelligence (AI) based deep learning module employed on the memory; and
   a console connected to the computer system and configured to display the ultrasound images acquired by the ultrasound probe;
   wherein a user selects a region within the ultrasound image that requires time gain compensation and wherein the AI based deep learning module is configured to carry out time gain compensation of the user selected region of the ultrasound image and display a time gain compensated image over the console.

15. The system of claim 14 wherein the AI based deep learning module identifies a texture of the user selected region and at least one region within the ultrasound image that exhibits a similar texture for carrying out time gain compensation.

16. The system of claim 14 wherein the AI based deep learning module is configured to identify a region from a set of training ultrasound images stored on a computer memory that exhibits the similar texture to that of the user selected region.

17. The system of claim 14 wherein the user selects the region within the ultrasound image by identifying the region within the ultrasound image that requires time gain compensation and clicking on the region using a cursor of the console.

18. The system of claim 14 wherein the gain compensated image is displayed on the console after the AI based deep learning module divides the ultrasound image into a plurality of grid portions and shifts the intensity mean of the plurality of the grid portions corresponding to the user selected region to match a lowest depth of the user selected region.

19. The system of claim 14 wherein the console is configured to display the acquired ultrasound image and the time gain compensated ultrasound image simultaneously.

* * * * *